(12) United States Patent
Stanley-Majors et al.

(10) Patent No.: US 10,340,042 B1
(45) Date of Patent: Jul. 2, 2019

(54) SYSTEM AND METHOD FOR CODING AND CHARGING OF CERTAIN MEDICAL PROCEDURES FOR A PATIENT USING A GRAPHICAL INTERFACE

(71) Applicant: MEDICAL ASSET MANAGEMENT, INC., Atlanta, GA (US)

(72) Inventors: Belinda Stanley-Majors, Atlanta, GA (US); Gary Burns, Atlanta, GA (US)

(73) Assignee: MEDICAL ASSET MANAGEMENT, INC., Atlanta, GA (US)

( * ) Notice: Subject to any disclaimer, the term of this patent is extended or adjusted under 35 U.S.C. 154(b) by 725 days.

(21) Appl. No.: 14/858,926

(22) Filed: Sep. 18, 2015

Related U.S. Application Data

(60) Provisional application No. 62/052,334, filed on Sep. 18, 2014.

(51) Int. Cl.
*G16H 40/20* (2018.01)
*G16H 10/20* (2018.01)

(52) U.S. Cl.
CPC ............. *G16H 40/20* (2018.01); *G16H 10/20* (2018.01)

(58) Field of Classification Search
CPC .............................. G16H 10/60; G16H 15/00
See application file for complete search history.

(56) References Cited

U.S. PATENT DOCUMENTS

| | | | |
|---|---|---|---|
| 2008/0004505 A1* | 1/2008 | Kapit | G16H 15/00 600/300 |
| 2009/0070140 A1* | 3/2009 | Morsch | G06Q 50/22 705/2 |

\* cited by examiner

*Primary Examiner* — Sheetal R Paulson
(74) *Attorney, Agent, or Firm* — Greenberg Traurig LLP

(57) ABSTRACT

Various illustrative embodiments of a system, method and related devices for coding of a medical procedure for a patient are disclosed. The disclosed subject matter seeks to improve the operational flow of hospital billing for medical procedures, including but not limited to those procedures generally performed in the cardiac catheterization laboratory, interventional or endovascular suite or hospital operating room such as those relating to interventional radiology, interventional cardiology, electrophysiology, vascular surgery, pacemakers and implantable defibrillators, and biliary and central venous access devices.

8 Claims, 11 Drawing Sheets

SYSTEM AND METHOD FOR CODING AND CHARGING OF CERTAIN MEDICAL PROCEDURES FOR A PATIENT USING A GRAPHICAL INTERFACE

RELATED APPLICATIONS

This application claims the benefit, and priority benefit, of U.S. Provisional Patent Application No. 62/052,334, filed on Sep. 18, 2014, the disclosure and contents of which are incorporated by reference herein in their entirety.

FIELD OF THE INVENTION

The presently disclosed subject matter relates to the field of medical coding, and more particularly, to a system and method for coding certain medical procedures for a patient using a graphical interface.

BACKGROUND

Procedure codes are used as a tool in the healthcare industry to describe surgical and non-surgical procedures performed in a clinical setting. Procedure coding is an industry-accepted uniform method of translating written descriptions of medical procedures, surgeries and treatment into specific alphanumeric codes for classification, specifically for tracking and billing purposes. These codes are commonly referred to as CPT codes, which are owned by the American Medical Association (AMA), for which this process makes no claim. The codes are typically assigned by a health professional trained in medical coding such as a clinical coder or Health Information Manager.

Various types of systems and related software have been provided to assist with procedural coding. Many of these systems are referred to as "encoders" and function as an electronic version of a procedural coding manual. For procedural coding of certain vascular procedures, the process of coding is complex and time consuming. For example, the user was often burdened with sifting through multiple drop-down lists of selections. Also, in previous systems used for coding procedures for a vascular system, each vessel's order had to be hard-coded for each access site, leading to hundreds of combinations of body systems that were mostly duplicates. Improvements in this field of technology are desired.

SUMMARY

Figure 1:
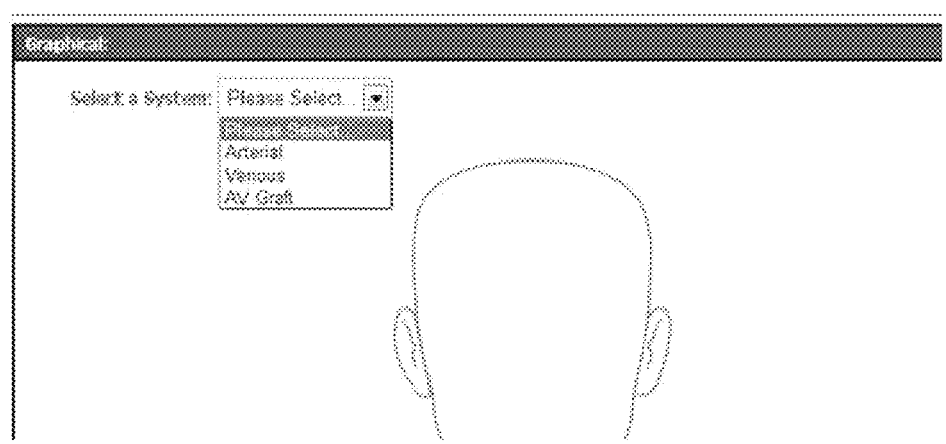
FIG. 1 is a diagram illustrating a software interface and screen layout setup for the disclosed subject matter in certain illustrative embodiments.

Disclosed herein are various illustrative embodiments of a system, method and related devices for coding of a medical procedure for a patient. The disclosed subject matter seeks to revolutionize the operational flow of hospital billing for medical procedures, including but not limited to those procedures generally performed in the cardiac catheterization laboratory, interventional or endovascular suite or hospital operating room such as those relating to interventional radiology, interventional cardiology, electrophysiology, vascular surgery, pacemakers and implantable defibrillators, and biliary and central venous access devices.

In certain illustrative embodiments, a method for coding of a medical procedure on a vascular system of a patient is provided. An identification of the category of vascular system on which the medical procedure will be performed is received from a user through a graphical interface of a computer device. In response to the identification of the category of vascular system, a graphical representation of the identified vascular system is generated and displayed on the graphical interface of the computer device. One or more access site options are generated and displayed on the graphical representation of the identified vascular system. A selection from the one or more access site options of an access site location is received from the user on the graphical representation of the identified vascular system and through the graphical interface of the computer device. In response to the selection of the access site location, a graphical representation of one or more vessel orders for the identified vascular system is generated and displayed on the graphical interface of the computer device. A selection of one or more catheterization locations is received from the user on the graphical representation of the identified vascular system and through the graphical interface of the computer device. In response to the selection of the one or more catheterization locations, a graphical representation of the one or more catheterization locations for the identified vascular system is generated and displayed on the graphical interface of the computer device. One or more medical codes for the medical procedure are generated using the one or more vessel orders and or one or more catheterization locations for the identified vascular system.

In certain aspects of the above described method, an instruction to identify one or more access site options can be received from the user through the graphical interface of the computer device prior to generating and displaying on the graphical representation of the identified vascular system the one or more access site options. Also, an instruction to identify one or more catheterization locations can be received from the user through the graphical interface of the computer device prior to generating and displaying on the graphical interface of the computer device a graphical representation of the one or more catheterization locations for the identified vascular system. In certain additional aspects of the above described method, the graphical representation of the identified vascular system can include an anatomical image of the patient with the identified vascular system associated therewith.

In certain illustrative embodiments, a computer program product for coding of a medical procedure on a vascular system of a patient can be provided. The program product can include a non-transitory computer readable storage medium. The storage medium can have stored thereon a plurality of program instructions executable by a computing device to cause the computing device to perform a plurality of tasks. For example, first program instructions executable by a computing device can cause the computing device to receive in the computing device from the user through a graphical interface an identification of the category of vascular system on which the medical procedure will be performed. Second program instructions executable by a computing device can cause the computing device to generate and display on the graphical interface of the computer device, in response to the identification of the category of vascular system, a graphical representation of the identified vascular system. Third program instructions executable by a computing device can cause the computing device to generate and display on the graphical representation of the identified vascular system one or more access site options. Fourth program instructions executable by a computing device can cause the computing device to receive from the user on the graphical representation of the identified vascular system and through the graphical interface of the computer device a selection of one or more access site locations from the one or more access site options. Fifth program instructions executable by a computing device can cause the computing device to generate and display on the graphical interface of the computer device, in response to the selection of the access site location, a graphical representation of one or more vessel orders for the identified vascular system. Sixth program instructions executable by a computing device can cause the computing device to receive from the user on the graphical representation of the identified vascular system and through the graphical interface of the computer device a selection of one or more catheterization locations. Seventh program instructions executable by a computing device can cause the computing device to generate and display on the graphical interface of the computer device, in response to the selection of one or more catheterization locations, a graphical representation of the one or more catheterization locations for the identified vascular system. Eighth program instructions executable by a computing device can cause the computing device to generate one or more medical codes for the medical procedure using the one or more vessel orders and/or one or more catheterization locations for the identified vascular system. Despite the use of numerical terms to describe the program instructions, it should be recognized that certain of the tasks described above may be omitted or performed in a different order without departing from the scope of the presently disclosed subject matter. In certain aspects, the computing device can be a mobile computing device.

In certain illustrative embodiments, a non-transitory computer-readable storage medium tangibly encoded with computer-executable instructions is provided, that when executed by a processor associated with a computing device, can perform a method that includes a plurality of steps. For example, an identification of the category of vascular system on which the medical procedure will be performed can be received from a user through a graphical interface of a computer device. In response to the identification of the category of vascular system, a graphical representation of the identified vascular system can be generated and displayed on the graphical interface of the computer device. One or more access site options can be generated and displayed on the graphical representation of the identified vascular system. A selection from the one or more access site options of an access site location can be received from the user on the graphical representation of the identified vascular system and through the graphical interface of the computer device. In response to the selection of the access site location, a graphical representation of one or more vessel orders for the identified vascular system can be generated and displayed on the graphical interface of the computer device. A selection of one or more catheterization locations can be received from the user on the graphical representation of the identified vascular system and through the graphical interface of the computer device. In response to the selection of the one or more catheterization locations, a graphical representation of the one or more catheterization locations for the identified vascular system can be generated and displayed on the graphical interface of the computer device. One or more medical codes for the medical procedure can be generated using the one or more vessel orders and/or one or more catheterization locations for the identified vascular system.

In certain illustrative embodiments, a system for coding of a medical procedure on a vascular system of a patient can be provided. The system can include a computing device having a processor and memory thereon for the storage of executable instructions and data. The instructions can be executed to perform a plurality of tasks. For example, the computing device can receive from the user through a graphical interface an identification of the category of vascular system on which the medical procedure will be performed. A graphical representation of the identified vascular system can be generated and displayed on the graphical interface of the computer device, in response to the identification of the category of vascular system. One or more access site options can also be generated and displayed on the graphical representation of the identified vascular system. A selection of one or more access site locations from the one or more access site options can be received from the user on the graphical representation of the identified vascular system and through the graphical interface of the computer device. A graphical representation of one or more vessel orders for the identified vascular system can be generated and displayed on the graphical interface of the computer device, in response to the selection of the access site location. The computing device can receive from the user on the graphical representation of the identified vascular system and through the graphical interface of the computer device a selection of one or more catheterization locations. A graphical representation of the one or more catheterization locations for the identified vascular system can be generated and displayed on the graphical interface of the computer device, in response to the selection of one or more catheterization locations. One or more medical codes for the medical procedure can be generated using the one or more vessel orders and or one or more catheterization locations for the identified vascular system.

DETAILED DESCRIPTION

Disclosed herein are various illustrative embodiments of a system, method and related devices for coding of a medical procedure for a patient. The disclosed subject matter seeks to improve the operational flow of hospital billing for medical procedures, including but not limited to those procedures generally performed in the cardiac catheterization laboratory, interventional or endovascular suite or hospital operating room such as those relating to interventional radiology, interventional cardiology, electrophysiology, vascular surgery, pacemakers and implantable defibrillators, and biliary and central venous access devices.

In certain illustrative embodiments, the disclosed subject matter relates to a software product and related system and method that can derive applicable hospital charge codes and/or current procedural terminology (CPT) and healthcare common procedure coding system (HCPCS) codes that describe procedures performed in the setting of the cardiac catheterization laboratory, interventional or endovascular suite or hospital operating room. The software product can utilize anatomical graphics that are more familiar to the user of the product (specifically radiologic technologists, physicians and other clinical professionals) so that these users can make graphical-based, "point-and-click" selections based on the clinical procedures being performed. Based on the graphical selections, the embedded intelligence of the product can be activated to display an output for the user. This information can be used to bill for the clinical procedures that are performed and eliminate several manual steps currently in place in existing systems for the operational flow for hospital billing.

In certain illustrative embodiments, the software product and related system and method can utilize modern web browsers along with highly advanced JavaScript and vector graphic rendering capabilities. Many technologies in HTML5 and CSS3, along with complex JavaScript for manipulating SVG (Scalable Vector Graphic) data, can be incorporated into the software product and related system and method to create a user interface that displays interactive graphical elements, rather than solely traditional web form elements (i.e., checkboxes, radio buttons, list boxes, etc.).

Many existing products for medical coding utilize a "page-by-page" process for coding an interventional radiology case. That is, through a series of prompts and questions, the user proceeds through each step of the case as a separate page, until all details of catheterization, diagnostic imaging, and therapeutic interventions are known. In certain illustrative embodiments, the presently disclosed software product and related system and method streamline this process into as few pages as possible, thus allowing the user to specify nearly all details of an interventional radiology case from, in some cases, a single page.

FIGS. 1-6 illustrate exemplary embodiments of software interfaces and screen layout setups for use on the computing devices that would be useful in this presently disclosed subject matter.

FIG. 1 illustrates an exemplary startup screen for a computing device according to the presently disclosed subject matter. The startup screen has a query box with a button signaling a drop down menu. The user begins by selecting the appropriate vascular system from the drop down list at the top of the page.

Figure 2:
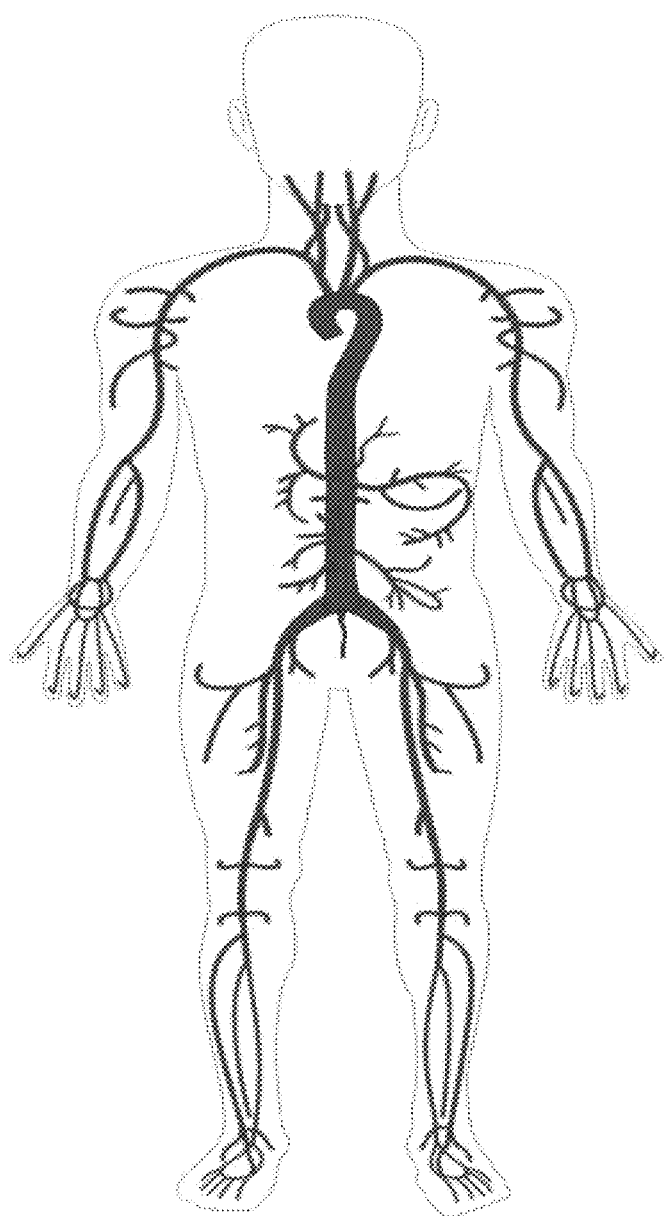
FIG. 2 is a diagram illustrating a software interface and screen layout setup for the disclosed subject matter in certain illustrative embodiments.

When the user selects the vascular system, the user is provided with the interface shown in FIG. 2, wherein all of the available vessels that can be coded in that system are automatically displayed on the screen.

Figure 3:
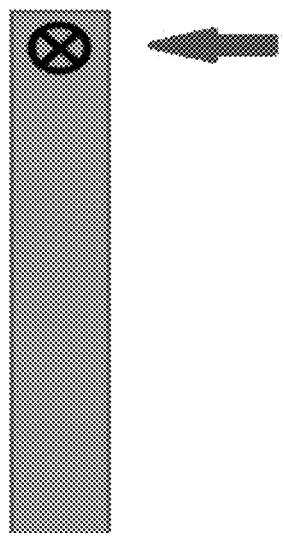
FIG. 3 is a diagram illustrating a software interface and screen layout setup for the disclosed subject matter in certain illustrative embodiments.
Figure 4:
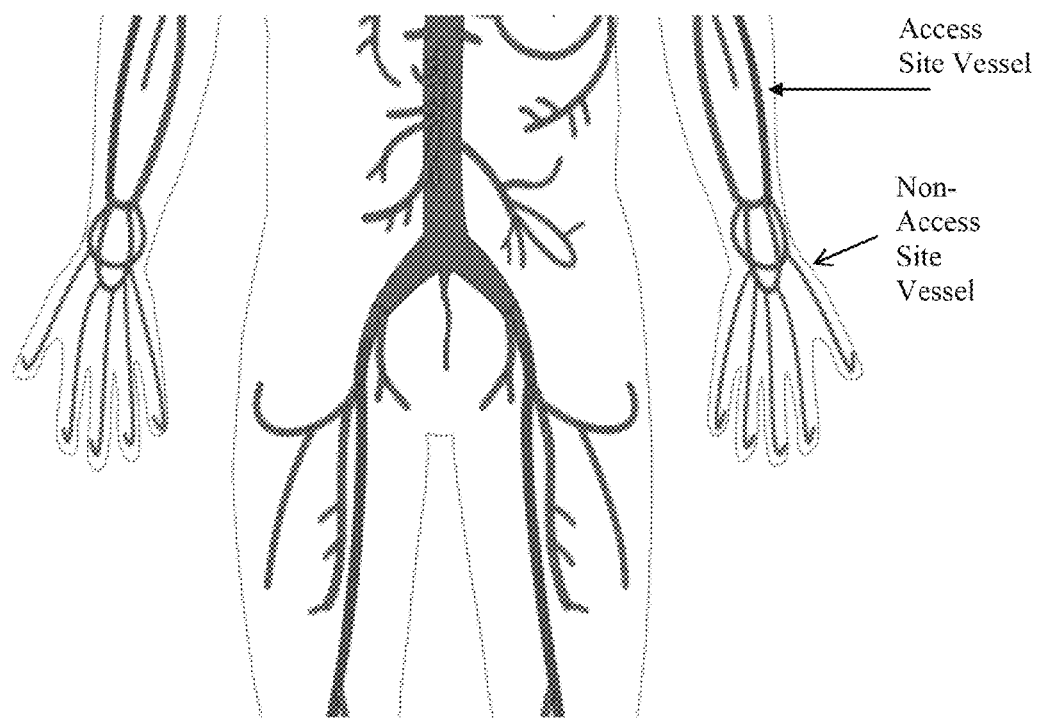
FIG. 4 is a diagram illustrating a software interface and screen layout setup for the disclosed subject matter in certain illustrative embodiments.

As shown in FIG. 3, the user can choose to utilize the "Insertion Site" tool from a side toolbar on the graphical display. Once this tool is selected, any vessels that are "access sites" become highlighted, while non-access site vessels are greyed out. The "access sites" can be highlighted in one or more identifying colors, in certain illustrative embodiments. The user can then select one of the access site vessels as an "access site" by touching or pointing and clicking on the vessel.

Figure 5:
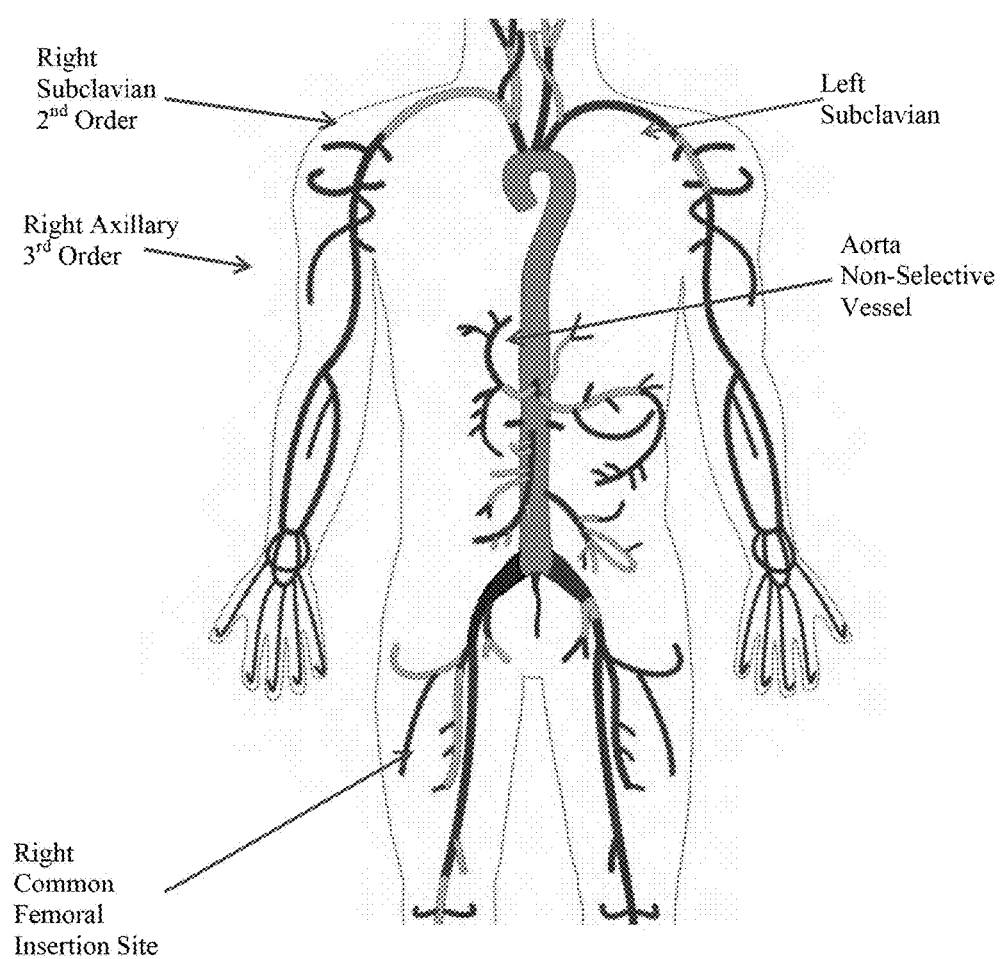
FIG. 5 is a diagram illustrating a software interface and screen layout setup for the disclosed subject matter in certain illustrative embodiments.

Once an access site is selected, the "order" of each vessel (indicated by color-coding) is automatically calculated by the system. The order of a vessel depends on which vessel is the access site, among other factors. The logic within the system computes the order for all vessels dynamically. For example, FIG. 5 depicts the insertion site for the right common femoral artery and typical arterial anatomy.

Figure 6:
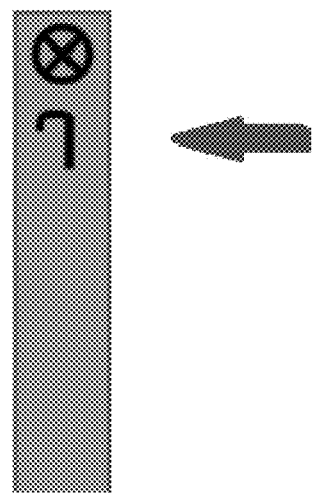
FIG. 6 is a diagram illustrating a software interface and screen layout setup for the disclosed subject matter in certain illustrative embodiments.

As illustrated in FIG. 6, the user can select the "Catheterization" tool from the side toolbar. Once this tool is selected, any vessel that the user touches or points and clicks on will be marked as catheterized by the system.

The system can then generate the correct CPT Code output for all catheterized vessels by using the previously calculated order of the selected vessels, along with complex coding logic that is built into the presently disclosed subject matter. The benefit of this dynamic calculation process is that the system can facilitate any combination of access site(s) and catheterized vessels, and still generate the correct output.

Figure 7:
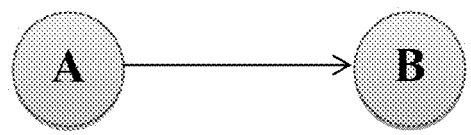
FIG. 7 is a diagram illustrating vessels represented as nodes in accordance with the disclosed subject matter in certain illustrative embodiments.

Describing the vascular system model on a high-level, the foundation of the presently disclosed system, according to certain illustrative embodiments, is the abstract representation of the major vessels found in the human vascular system through the use of mathematical graph theory. The actual vessels in the human body branch outward from the heart, splitting into smaller vessels the farther into the extremities they go. This anatomical characteristic can be described using the same qualities and principles common in graph theory. More specifically, the vascular system can be represented as a connected directional tree. Each vessel is treated as a node within this tree, with an edge connecting it to another node if those two vessels are adjacent to one another in the body. For example, if Vessel "B" branches from Vessel "A", there are two nodes {A, B} and one edge {AB}, with the directionality of the edge going from node "A" to node "B". See, for example, FIG. 7 herein.

An important detail of the tree structure, according to certain illustrative embodiments, is that each node must have one, and only one incoming edge. In other words, a vessel can only branch from one "parent" vessel. This prevents any cycles from being in the graph (which is required of a tree), and also provides that there is exactly one unique path between any two vessels. To find this path, there are many well-established algorithms. In certain illustrative embodiments of the presently disclosed subject matter, a breadth-first-search (BFS) is used. This forms the basis of how all of the vessels within the vascular model can be traversed through catheterization.

As to a database model, the vascular system model's actual implementation occurs within a standard SQL database, according to certain illustrative embodiments. The tables in the schema represent both the vascular system graph (nodes and edges) as well as the particular views and anatomy details present in the human body.

Figure 9:
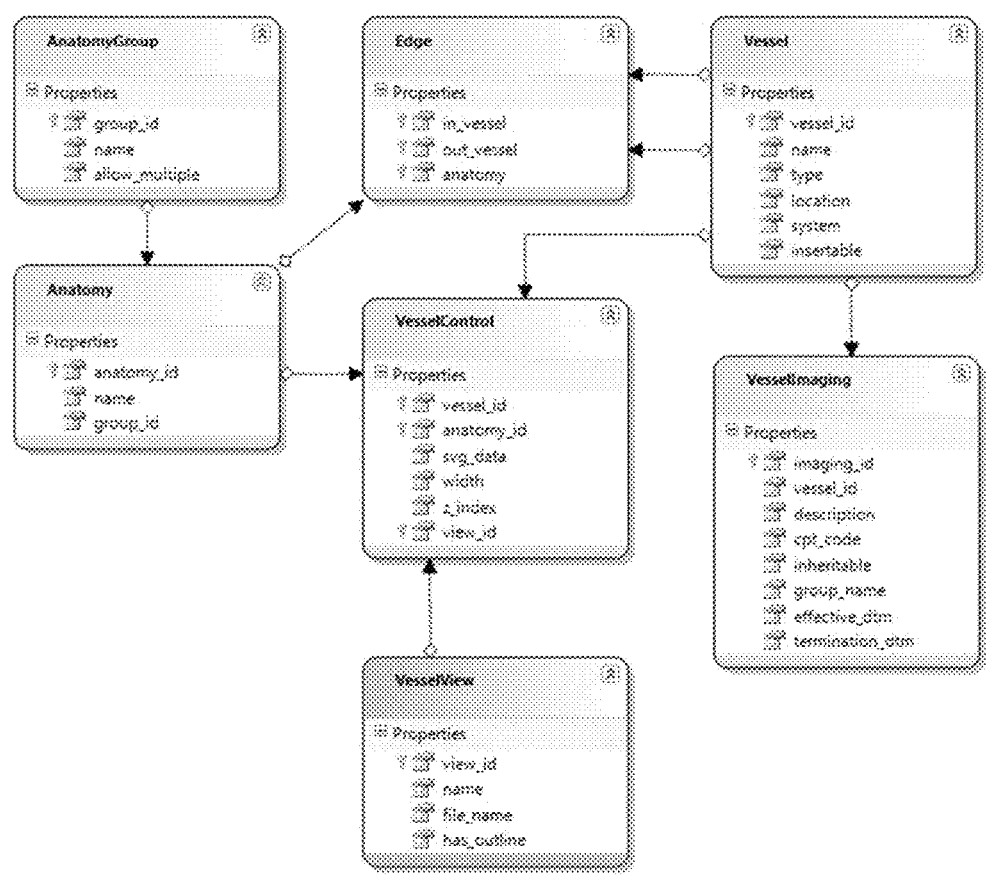
FIG. 9 is a system diagram in accordance with the disclosed subject matter in certain illustrative embodiments.

See, for example, the database entity relationship (or "ER") diagram in FIG. 9 herein with the following table descriptions:

Vessel: Basic descriptors of a vessel. Name, location in body, etc.

Edge: Defines the connections between all vessels in specified anatomy.

Anatomy: Collection of common anatomical variations within vascular system.

Anatomy Group: Groups the anatomical variations by their location/system.

Vessel Control: Contains all information required to draw the vessel in the UI.

Vessel View: Defines different vantage points, e.g., abdominal, intracranial, etc.

Vessel Imaging: Defines what types of imaging is available for this vessel.

As to an application model, the application model is written in C# as part of an ASP.NET web application, according to certain illustrative embodiments. This portion of the software can contain all of the interventional coding logic to correctly determine catheterization codes for any vascular procedure.

According to certain illustrative embodiments, the application model takes as input an "insertion site" (or starting point within the vascular system graph) and any number of selected vessels in the graph. Given the pre-loaded database model of the vascular system, it then uses a breadth-first-search to calculate the unique path from the insertion site to each vessel that was catheterized. Any path which is a sub-path of another can be discarded due to the fact that the longer path would take precedence. For example, if the application model had two paths {A B C} and {A B C D}, it would discard the first one because it is contained in the second one. Finally, with the remaining paths, the "order" of each is calculated. The order is essentially the number of nodes away from the center of the graph that the final node sits. The order directly corresponds to the appropriate output code for that path. The application model has the capability of calculating the catheterization codes for multiple insertion sites by using the above method for each one independently.

As to a graphical model, the user interface for the presently disclosed subject matter can utilize HTML5 and Javascript technologies to create an interactive model of the human body. The model can consist of various views (full body, intracranial, extracranial, abdominal, etc.) of both the arterial and venous portions of the vascular system. Through the use of the open-source KineticJS library and the SVG capabilities of the HTML5 canvas element, each vessel is drawn to the screen as an object that supports all common mouse events, in certain illustrative embodiments. The SVG data for each vessel can be stored in read-only mode in the database along with the logical components of the vascular data structure. Also included in the UI is a toolbar with an element to select insertion sites and an element to select catheterized vessels.

Once the page containing the graphical model is loaded from the server, almost all interaction with the interface occurs through asynchronous mechanisms. For example, to select an insertion site from the visible vessels in the view, the user would select the insertion site tool from the toolbar. When selected, a Javascript function highlights only those vessels that are eligible to be insertion sites. If the user clicks on one of these vessels, an AJAX call is made back to the application model to set this as the initial insertion site. Additionally, the application model then pre-calculates the order of each vessel in the vascular system, and returns an XML response containing this data. Once the insertion site is selected, a user can then select vessels that were catheterized from this starting point simply by clicking on each one using the catheterization tool from the toolbar. For each vessel clicked, an AJAX call is sent back to the application model to set these vessels as having been catheterized. From the user's point of view, the page behaves as a seamless interactive application that never needs to reload or advance to a subsequent page.

Figure 8:
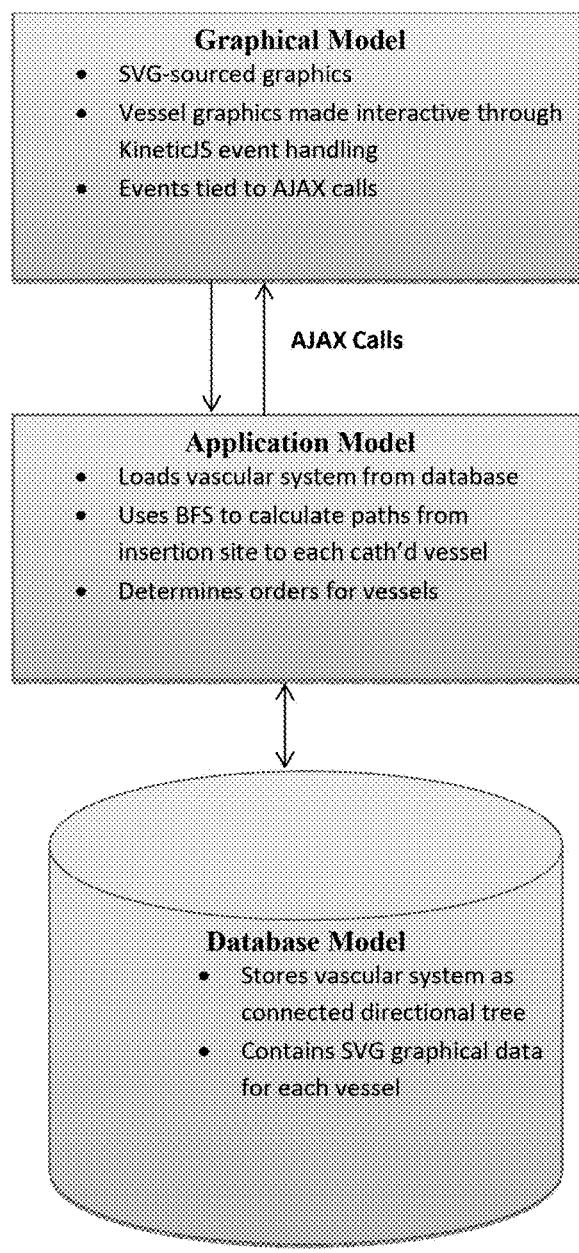
FIG. 8 is a database entity relationship (or "ER") diagram in accordance with the disclosed subject matter in certain illustrative embodiments.
Figure 10:
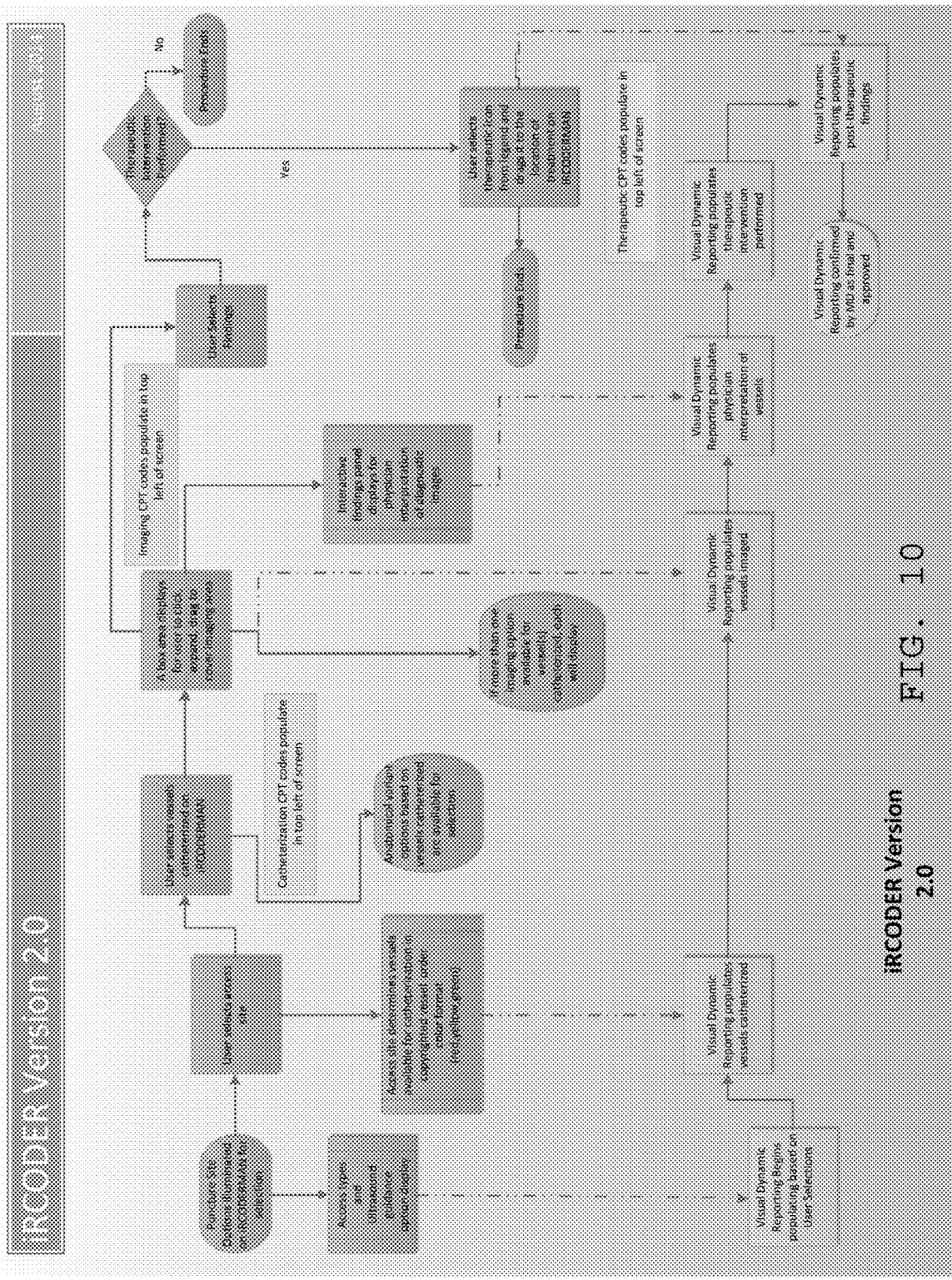
FIG. 10 is a flowchart illustrating steps performed in accordance with the disclosed subject matter in certain illustrative embodiments.

A system diagram according to an illustrative embodiment of the disclosed subject matter is shown in FIG. 8 herein. A flowchart relating to an illustrative embodiment of the disclosed subject matter is shown in FIG. 10 herein.

The various illustrative embodiments disclosed herein provide significant advantages over prior art systems and methods. For example, the dynamic code generation of the presently disclosed subject matter is a significant improvement over previous vascular modules. With the older modules, each vessel's order had to be hard-coded for each access site, leading to hundreds of combinations of body systems that were mostly duplicates. With the presently disclosed subject matter, the user is no longer burdened with sifting through multiple dropdown lists of selections. Instead, they can simply touch or point and click on the graphics associated with the system. Further, the presently disclosed subject matter differs from what is known or used before in this field in that prior art systems were not activated by use of anatomical illustrations. In the presently disclosed subject matter, the user can activate the intelligence of the product by accessing labeled vessels on an anatomical graphic. The selection of vessels communicates to the software and generates CPT code output based on medical coding guidelines. The codes output by the software can be used by hospitals to bill insurance for reimbursement of services.

Figure 11:
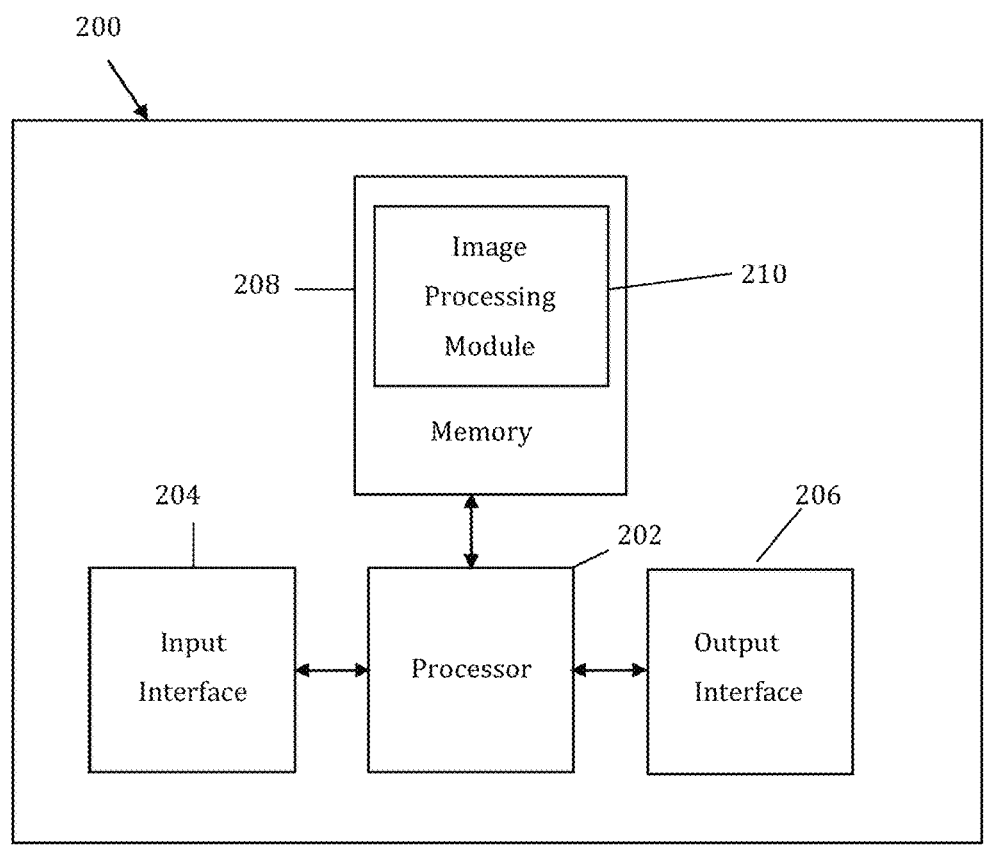
FIG. 11 is a block diagram of a computer system as may be utilized for the disclosed subject matter in certain illustrative embodiments While certain preferred illustrative embodiments will be described herein, it will be understood that this description is not intended to limit the subject matter to those embodiments. On the contrary, it is intended to cover all alternatives, modifications, and equivalents, as may be included within the spirit and scope of the subject matter as defined by the appended claims.

FIG. 11 is a schematic diagram of an embodiment of a system 200 that may correspond to or may be part of a computer and/or any other computing device, such as a workstation, server, mainframe, super computer, and/or portable computing device. The system 200 can comprise a processor 202, which may be also be referenced as a central processor unit (CPU). The processor 202 may communicate (e.g., via a system bus) and/or provide instructions to other components within the system 200, such as the input interface 204, output interface 206, and/or memory 208. In one embodiment, the processor 202 may comprise one or more multi-core processors and/or memory mediums (e.g., cache memory) that function as buffers and/or storage for data. Additionally, processor 202 may be part of one or more other processing components, such as application specific integrated circuits (ASICs), field-programmable gate arrays (FPGAs), and/or digital signal processors (DSPs). Although FIG. 11 illustrates that processor 202 may be a single processor, processor 202 is not so limited and instead may represent a plurality of processors. The processor 202 may be configured to implement any of the methods described herein.

FIG. 11 illustrates that memory 208 may be operatively coupled to processor 202. Memory 208 may be a non-transitory medium configured to store various types of data. For example, memory 208 may include one or more memory devices that comprise secondary storage, read-only memory (ROM), and/or random-access memory (RAM). The secondary storage is typically comprised of one or more disk drives, optical drives, solid-state drives (SSDs), and/or tape drives and is used for non-volatile storage of data. In certain instances, the secondary storage may be used to store overflow data if the allocated RAM is not large enough to hold all working data. The secondary storage may also be used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store instructions.

As shown in FIG. 11, the memory 208 may be used to house the instructions for carrying out various embodiments described herein. In an embodiment, the memory 208 may comprise an application 210 that may be accessed and implemented by processor 202. Additionally or alternatively, application 210 may be stored and accessed within memory embedded in processor 202 (e.g., cache memory). The application 210 may be configured to provide computer executable instructions used for the presently disclosed subject matter. In one embodiment, memory 208 may interface with a system bus (e.g., a computer bus) so as to communicate and/or transmit information stored in memory 208 to processor 202 during execution of software programs, such as software applications that comprise program code, and/or computer executable process steps that incorporate functionality described herein (e.g., the application 210).

Persons of ordinary skill in the art are aware that software programs may be developed, encoded, and compiled in a variety computing languages for a variety software platforms and/or operating systems and subsequently loaded and executed by processor 202. In one embodiment, the compiling process of the software program, (e.g., application 210), may transform program code written in a programming language to another computer language such that the processor 202 is able to execute the programming code. For example, the compiling process of the software program may generate an executable program that provides encoded instructions (e.g., machine code instructions) for processor 202 to accomplish specific, non-generic, particular computing functions.

After the compiling process, the application 210 may then be loaded as computer executable instructions or process steps to processor 202 from storage (e.g., memory 208, storage medium/media, removable media drive, and/or other storage device) and/or embedded within the processor 202. Processor 202 can execute the stored instructions or process steps in order to perform instructions or process steps to transform the computing system 200 into a non-generic, particular, specially programmed machine or apparatus. Stored data, e.g., data stored by a storage device, can be accessed by processor 202 during the execution of computer executable instructions or process steps to instruct one or more components within the computing system 200.

Alternatively, rather than programming and/or loading executable instructions onto memory 208 and/or processor 202 to form a non-generic, particular machine or apparatus, persons of ordinary skill in the art are aware that stored instructions may be converted and implemented as hardware customized for a particular use. In one embodiment, implementing instructions by loading executable software into a computing device, can be converted to a hardware implementation by well-known design rules. For example, the compiling process of the software program 210 may build a sequence of instruction bits that control and arrange a sequence of control gate-level components that write data onto buses, into latches and registers, across channels, memory, and/or other components of the processor 202 and/or memory 208. The compiling of the application 210 may produce gate-level components with fixed relationships designed to accomplish specific, non-generic, particular computing functions using an algorithm.

The decisions between implementing a concept in software versus hardware may depend on a number of design choices that include stability of the design and numbers of units to be produced and issues involved in translating from the software domain to the hardware domain. Often a design may be developed and tested in a software form and subsequently transformed, by well-known design rules, to an equivalent hardware implementation in an ASIC or other application specific hardware that hardwires the instructions or process steps of the software. In the same manner as a machine controlled by a new ASIC is a non-generic, particular, specially programmed machine or apparatus, likewise a computing device (e.g., a computer) that has been programmed and/or loaded with executable instructions or process steps (e.g., the computing system 210) should be viewed as a non-generic, particular, specially programmed machine or apparatus.

FIG. 11 also illustrates that the processor 202 may be operatively coupled to an input interface 204 configured to receive data and output interface 206 configured to output and/or display data and/or information. The input interface 204 may be configured to obtain the data via cables, connectors, wireless connections and/or other communication protocols. In one embodiment, the input interface 202 may be a network interface that comprises a plurality of ports configured to receive and/or transmit data via a network. In particular, the network interface may transmit the data via wired links, wireless link, and/or logical links. Other examples of the input interface 204 may be universal serial bus (USB) interfaces, CD-ROMs, DVD-ROMs and/or connections to one or more receivers. The output interface 206 may include, but is not limited to one or more connections for a graphic display (e.g., monitors), a printing device that produces hard-copies of the generated results, and/or a plurality of ports that transmit data via cables, connectors, wireless connections, and/or other communication protocols.

Persons of ordinary skill in the art are aware that the system 200 may comprise other components well known in the art, such as sensors, powers sources, and/or analog-to-digital converters, not explicitly shown in FIG. 11. For ease of discussion, FIG. 11 may exclude other common or typical components known by persons of ordinary skill in the art.

Those skilled in the art will also appreciate that portions of the subject matter disclosed herein may be embodied as a method, data processing system, or computer program product. Accordingly, these portions of the subject matter disclosed herein may take the form of an entirely hardware embodiment, an entirely software embodiment, or an embodiment combining software and hardware. Furthermore, portions of the subject matter disclosed herein may be a computer program product on a computer-usable storage medium having computer readable program code on the medium. Any suitable computer readable medium may be utilized including hard disks, CD-ROMs, optical storage devices, or other storage devices.

The system and method can include at least one computer readable medium or alternatively, the computer readable medium may be accessed through various paths, such as networks, internet, drives, etc. Examples of computer readable media are compact discs, hard disks, floppy disks, tape, magneto-optical disks, PROMs (EPROM, EEPROM, Flash, EPROM), DRAM, SRAM, SDRAM, etc. Stored on any one or on a combination of computer readable media, the presently disclosed subject matter includes software for controlling both the hardware of the computer and for enabling the computer to interact with a human user. Such software may include, but is not limited to, device drivers, operating systems and user applications such as development tools. Such computer readable media further includes the computer program product of the presently disclosed subject matter for performing any of the methods according to the presently disclosed subject matter.

Consistent with the presently disclosed subject matter, the computer program code for carrying out operations of the presently disclosed subject matter may also be written in conventional procedural programming languages such as ASP (Active Server Pages), HTML (Hypertext Markup Language), SQL (Structured Query Language), and C++.

A user may enter commands and information into the computer through one or more user input devices, such as a touchscreen, keyboard and/or a pointing device (e.g., a mouse). Other input devices (not shown) may include a microphone, a joystick or the like. These and other input devices are often connected to the processing unit through a serial port interface that is coupled to the system bus, but may be connected by other interfaces, such as a parallel port or a universal serial bus (USB). A monitor or other type of display device can also be connected to the system bus via an interface, such as a video adapter. In addition to the monitor, the computer may include other peripheral output devices (not shown), such as speakers, printers, etc.

The present disclosure is described with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of a general purpose computer, special purpose computer, ASIC, or other programmable data processing apparatus, such that the instructions, which execute via the processor of the computer or other programmable data processing apparatus, implement the functions/acts specified in the block diagrams or operational block or blocks.

For the purposes of this disclosure a computer readable medium (or computer-readable storage medium/media) stores computer data, which data can include computer program code (or computer-executable instructions) that is executable by a computer, in machine-readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Various templates and the database(s) according to the presently disclosed subject matter may be stored locally on a provider's stand-alone computer terminal (or computing device), such as a desktop computer, laptop computer, palmtop computer, or personal digital assistant (PDA) or the like. Exemplary stand-alone computers may include, but are not limited to, Apple®, Sun Microsystems®, IBM®, or IBM®-compatible personal computers. Accordingly, the present invention may be carried out via a single computer system, such as a desktop computer, laptop computer, tablet device, smart phone, etc . . . .

The subject matter described herein may be embodied as methods, devices, components, or systems. Accordingly, embodiments may, for example, take the form of hardware, software, firmware or any combination thereof (other than software per se). The present detailed description is, therefore, not intended to be taken in a limiting sense.

Throughout the specification and claims, terms may have nuanced meanings suggested or implied in context beyond an explicitly stated meaning. Likewise, the phrase "in one embodiment" and the like as used herein does not necessarily refer to the same embodiment and the phrase "in another embodiment" and the like as used herein does not necessarily refer to a different embodiment. It is intended, for example, that claimed subject matter include combinations of example embodiments in whole or in part.

For the purposes of this disclosure, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly. A wireless network may further employ a plurality of network access technologies, including Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a client (or consumer or user) device may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device an Near Field Communication (NFC) device, a Personal Digital Assistant (PDA), a handheld computer, a tablet computer, a laptop computer, a set top box, a wearable computer, an integrated device combining various features, such as features of the forgoing devices, or the like.

A client device may vary in terms of capabilities or features. The claimed subject matter is intended to cover a wide range of potential variations. For example, a cell phone may include a numeric keypad or a display of limited functionality, such as a monochrome liquid crystal display (LCD) for displaying text. In contrast, however, as another example, a web-enabled client device may include one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A client device may include or may execute a variety of operating systems, including a personal computer operating system, such as a Windows, iOS or Linux, or a mobile operating system, such as iOS, Android, or Windows Mobile, or the like. A client device may include or may execute a variety of possible applications, such as a client software application enabling communication with other devices, such as communicating one or more messages, such as via email, short message service (SMS), or multimedia message service (MMS), including via a network, such as a social network, including, for example, Facebook®, LinkedIn®, Twitter®, Flickr®, or Google+®, Instagram™, to provide only a few possible examples. A client device may also include or execute an application to communicate content, such as, for example, textual content, multimedia content, or the like. A client device may also include or execute an application to perform a variety of possible tasks, such as browsing, searching, playing various forms of content, including locally stored or streamed video. The foregoing is provided to illustrate that claimed subject matter is intended to include a wide range of possible features or capabilities.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter. Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the appended claims.

What is claimed is:

1. A computer implemented method for coding of a medical procedure for a vascular system of a patient, the method comprising:

imaging on a graphical interface of a computer device a query box, wherein the query box displays a plurality of categories of vascular systems for identification of the category of vascular system on which the medical procedure will be performed;

receiving from a user through the graphical interface of the computer device an identification of the category of vascular system on which the medical procedure will be performed;

in response to the identification of the category of vascular system, generating and displaying on the graphical interface of the computer device a graphical representation of the identified vascular system;

generating and displaying on the graphical representation of the identified vascular system one or more access site options;

receiving from the user on the graphical representation of the identified vascular system and through the graphical interface of the computer device a selection from the one or more access site options of an access site location;

in response to the selection of the access site location, generating and displaying on the graphical interface of the computer device a graphical representation of one or more vessel orders for the identified vascular system;

receiving from the user on the graphical representation of the identified vascular system and through the graphical interface of the computer device a selection of one or more catheterization locations;

in response to the selection of the one or more catheterization locations, generating and displaying on the graphical interface of the computer device a graphical representation of the one or more catheterization locations for the identified vascular system, wherein the one or more vessel orders and the one or more catheterization locations are generated by (i) determining an insertion site based on the selected access site location, (ii) calculating a path from the insertion site to each vessel to be catherized using a breadth first search, wherein the path contains one or more primary paths and one or more sub-paths, (iii) discarding any sub-path that is contained within a longer primary path, to produce a remaining catheterization location path, and (iv) determining the vessel order of the remaining catheterization location path based upon, when each vessel is treated as a node, the number of nodes away from the center of the graphical representation that the furthest node sits; and generating one or more medical codes for the medical procedure using the one or more vessel orders and or one or more catheterization locations for the identified vascular system.

2. The method of claim 1, further comprising receiving from the user through the graphical interface of the computer device an instruction to identify one or more access site options prior to generating and displaying on the graphical representation of the identified vascular system the one or more access site options.

3. The method of claim 1, further comprising receiving from the user through the graphical interface of the computer device an instruction to identify one or more catheterization locations prior to generating and displaying on the graphical interface of the computer device a graphical representation of the one or more catheterization locations for the identified vascular system.

4. The method of claim 1, wherein the graphical representation of the identified vascular system comprises an anatomical image of the patient with the identified vascular system associated therewith.

5. The method of claim 1, wherein the anatomical image of the patient with the identified vascular system associated therewith is color coded.

6. A computer program product for coding of a medical procedure on a vascular system of a patient, said computer program product comprising:

a non-transitory computer readable storage medium having stored thereon:

first program instructions executable by a computing device to cause the computing device to image on a graphical interface of a computer device a query box, wherein the query box displays a plurality of categories of vascular systems for identification of the category of vascular system on which the medical procedure will be performed;

second program instructions executable by a computing device to cause the computing device to receive in the computing device from the user through the graphical interface an identification of the category of vascular system on which the medical procedure will be performed;

third program instructions executable by a computing device to cause the computing device to generate and display on the graphical interface of the computer device, in response to the identification of the category of vascular system, a graphical representation of the identified vascular system;

fourth program instructions executable by a computing device to cause the computing device to generate and display on the graphical representation of the identified vascular system one or more access site options;

fifth program instructions executable by a computing device to cause the computing device to receive from the user on the graphical representation of the identified vascular system and through the graphical interface of the computer device a selection of one or more access site locations from the one or more access site options;

sixth program instructions executable by a computing device to cause the computing device to generate and display on the graphical interface of the computer device, in response to the selection of the access site location, a graphical representation of one or more vessel orders for the identified vascular system;

seventh program instructions executable by a computing device to cause the computing device to receive from the user on the graphical representation of the identified vascular system and through the graphical interface of the computer device a selection of one or more catheterization locations;

eighth program instructions executable by a computing device to cause the computing device to generate and display on the graphical interface of the computer device, in response to the selection of one or more catheterization locations, a graphical representation of the one or more catheterization locations for the identified vascular system, wherein the one or more vessel orders and the one or more catheterization locations are generated by (i) determining an insertion site based on the selected access site location, (ii) calculating a path from the insertion site to each vessel to be catherized using a breadth first search, wherein the path contains one or more primary paths and one or more sub-paths, (iii) discarding any sub-path that is contained within a longer primary path, to produce a remaining catheterization location path, and (iv) determining the vessel order of the remaining catheterization location path based upon, when each vessel is treated as a node, the number of nodes away from the center of the graphical representation that the furthest node sits; and ninth program instructions executable by a computing device to cause the computing device to generate one or more medical codes for the medical procedure using the one or more vessel orders and or one or more catheterization locations for the identified vascular system.

7. A non-transitory computer-readable storage medium tangibly encoded with computer-executable instructions, that when executed by a processor associated with a computing device, performs a method comprising:

imaging on a graphical interface of the computer device a query box, wherein the query box displays a plurality of categories of vascular systems for identification of the category of vascular system on which the medical procedure will be performed;

receiving in the computing device from the user through the graphical interface an identification of the category of vascular system on which the medical procedure will be performed;

generating and displaying on the graphical interface of the computer device, in response to the identification of the category of vascular system, a graphical representation of the identified vascular system;

generating and displaying on the graphical representation of the identified vascular system one or more access site options;

receiving from the user on the graphical representation of the identified vascular system and through the graphical interface of the computer device a selection of one or more access site locations from the one or more access site options;

generating and displaying on the graphical interface of the computer device, in response to the selection of the access site location, a graphical representation of one or more vessel orders for the identified vascular system;

receiving from the user on the graphical representation of the identified vascular system and through the graphical interface of the computer device a selection of one or more catheterization locations;

generating and displaying on the graphical interface of the computer device, in response to the selection of one or more catheterization locations, a graphical representation of the one or more catheterization locations for the identified vascular system, wherein the one or more vessel orders and the one or more catheterization locations are generated by (i) determining an insertion site based on the selected access site location, (ii) calculating a path from the insertion site to each vessel to be catherized using a breadth first search, wherein the path contains one or more primary paths and one or more sub-paths, (iii) discarding any sub-path that is contained within a longer primary path, to produce a remaining catheterization location path, and (iv) determining the vessel order of the remaining catheterization location path based upon, when each vessel is treated as a node, the number of nodes away from the center of the graphical representation that the furthest node sits; and generating one or more medical codes for the medical procedure using the one or more vessel orders and or one or more catheterization locations for the identified vascular system.

8. A system for coding of a medical procedure on a vascular system of a patient, comprising:

a computing device having a processor and memory thereon for the storage of executable instructions and data, wherein the instructions are executed to:

receive in the computing device from the user through a graphical interface an identification of the category of vascular system on which the medical procedure will be performed;

generate and display on the graphical interface of the computer device, in response to the identification of the category of vascular system, a graphical representation of the identified vascular system;

generate and display on the graphical representation of the identified vascular system one or more access site options;

receive from the user on the graphical representation of the identified vascular system and through the graphical interface of the computer device a selection of one or more access site locations from the one or more access site options;

generate and display on the graphical interface of the computer device, in response to the selection of the access site location, a graphical representation of one or more vessel orders for the identified vascular system;

receive from the user on the graphical representation of the identified vascular system and through the graphical interface of the computer device a selection of one or more catheterization locations;

generate and display on the graphical interface of the computer device, in response to the selection of one or more catheterization locations, a graphical representation of the one or more catheterization locations for the identified vascular system, wherein the one or more vessel orders and the one or more catheterization locations are generated by (i) determining an insertion site based on the selected access site location, (ii) calculating a path from the insertion site to each vessel to be catherized using a breadth first search, wherein the path contains one or more primary paths and one or more sub-paths, (iii) discarding any sub-path that is contained within a longer primary path, to produce a remaining catheterization location path, and (iv) determining the vessel order of the remaining catheterization location path based upon, when each vessel is treated as a node, the number of nodes away from the center of the graphical representation that the furthest node sits; and generate one or more medical codes for the medical procedure using the one or more vessel orders and or one or more catheterization locations for the identified vascular system.

\* \* \* \* \*